United States Patent [19]
Gould et al.

[11] Patent Number: 5,569,342
[45] Date of Patent: Oct. 29, 1996

[54] METHOD FOR PREPARING SOLID SURFACES FOR INSPECTION

[75] Inventors: Ronald W. Gould, Kemptville; Jerzy P. Komorowski, Gloucester, both of Canada

[73] Assignee: National Research Council of Canada, Ottawa, Canada

[21] Appl. No.: 295,475

[22] Filed: Aug. 25, 1994

Related U.S. Application Data

[63] Continuation-in-part of Ser. No. 18,225, Feb. 16, 1993, abandoned.

[51] Int. Cl.[6] .......................... B32B 31/04; G01N 21/00; G01B 11/30
[52] U.S. Cl. .......................... 156/64; 156/84; 156/273.1; 156/285; 356/237; 356/371
[58] Field of Search ............... 356/36, 237, 239, 356/371, 372, 430; 156/64, 285, 273.1, 379, 382, 499

[56] References Cited

U.S. PATENT DOCUMENTS

| | | | |
|---|---|---|---|
| 3,185,022 | 5/1965 | Holeman | 356/371 X |
| 3,519,362 | 7/1970 | Cardno et al. | 356/237 |
| 4,456,374 | 6/1984 | Langberg | 356/237 |
| 4,571,542 | 2/1986 | Arai | 338/114 X |
| 4,664,514 | 5/1987 | Corby, Jr. | 356/237 X |
| 5,039,225 | 8/1991 | Uekusa | 356/239 X |
| 5,076,691 | 12/1991 | Tullis et al. | 356/237 |

FOREIGN PATENT DOCUMENTS

0514182  11/1992  European Pat. Off. .
2164161   3/1986  United Kingdom .

OTHER PUBLICATIONS

"Condom takes fingerprint impression," The Engineer, Feb. 11, 1993 p. 32.

Primary Examiner—David A. Simmons
Assistant Examiner—M. Curtis Mayes
Attorney, Agent, or Firm—Juliusz Szereszewski

[57] ABSTRACT

Optical inspection techniques often require highlighting of the surface to inspected. A method and apparatus is provided to prepare such surfaces for instrumental inspection by applying a sheet of a solid, deformable film, e.g. a polymeric film or a metal foil, to the surface and then forcing the layer against the surface in a controlled manner so that a contiguous relationship therebetween is attained. The film can bridge pores, roughness and equalize the reflectivity of the surface. The film can usually be removed and reused without affecting the object.

5 Claims, 3 Drawing Sheets

METHOD FOR PREPARING SOLID SURFACES FOR INSPECTION

This application is a continuation-in-part, of application Ser. No. 08/018,225, filed Feb. 16, 1993, now abandoned.

FIELD OF THE INVENTION

This invention relates to a method and apparatus for preparing surfaces of solid objects to render the objects more suitable for instrumental inspection, particularly an inspection using optical instruments and techniques. In a specific aspect, this invention provides a method and apparatus for temporary preparation of the surfaces for the above purposes.

BACKGROUND OF THE INVENTION

Several inspection techniques are employed to scan, detect, assess and otherwise analyze the shape and surface characteristics of a solid object. Those techniques and in particular optical inspection techniques often require specialized preparation of a surface, or surfaces, of a solid object to be inspected. A number of factors can affect the optical inspection results, namely roughness, reflectivity, coloration, porosity and physical continuity. Not all those factors are essential in non-optical inspection methods.

By way of example, optical inspection techniques such as Shadow and Projection Moiré, Laser Shearography, Diffracto Sight, Back-Lighted Grid and Laser Beam Scanning require highlighting of the surface to be inspected to obtain its suitable reflectivity. It is known to modify surfaces to be inspected with specific liquid, paint or powder highlighters. This approach has the following drawbacks:

the highlighters are often solvent based and thus not environmentally neutral;

application problems (liquid-surface wetting, distribution and evaporation, non-uniformity of coverage);

removal problems (highlighters can be absorbed into the surface which may require additional removal processes and result in contaminated waste products);

evaporation rate of some highlighters restricts the duration of the inspection and lowers inspection repeatability;

incompatibility with inspected material (adverse effect on the inspected surface);

surface coloration read-through (non-uniform surface coloration may affect the inspection results);

porous materials cannot be inspected with liquid highlighters;

temperature dependence—evaporation of some highlighters;

surface contaminants may affect highlighting quality;

difficulty in controlling the surface roughness;

non-reusability.

SUMMARY OF THE INVENTION

It is an object of the invention to eliminate at least some of the above drawbacks by providing a method of modifying certain properties of the surface of a solid object to be inspected.

According to the invention, there is provided a method of preparing the surface of a solid object for instrumental inspection, the method comprising a) applying a layer of a solid, deformable film to at least a part of the surface to be inspected, and b) bringing the layer and the surface or the part thereof into a controlled contiguous relationship.

The contiguous relationship is controlled in a manner enabling the contiguity to remain unchanged for a time required for the inspection of the surface or its part.

The film is preferably of a uniform thickness, subject to some thickness changes due to the stretching associated with the method of the invention i.e. forcing against the subject surface.

In a particular embodiment of the invention, the contiguity is achieved by external positive pressure applied onto the film.

In another embodiment of the invention, the contiguity is achieved by negative pressure applied between the film and the surface. Obviously, in the two above cases, the film should be virtually free of perforations.

Alternatively, the film may be held in position by way of a permanent or releasable adhesive, by shrink-wrapping, static electrical attraction and other comparable methods. It is generally preferable to be able to remove the film after inspection thus bringing the inspected object to its original condition. An added benefit of the invention is a possibility, in some instances, of reusing the solid film. For the above embodiments, the film may be perforated.

The use of adhesive for maintaining the film/surface position during inspection may take place by the use of films with adhesive backing or through a separate adhesive layer placed between the film and the surface.

For inspection purposes where uniform reflectivity of the inspected surface is desired, a solid film of uniform reflectivity can be applied.

The method of the invention may use solid films designed to contain a texture or embossing to increase the background noise or to superimpose a periodic signal on the image of the surface. The background noise may be made to be uniform or varied through the solid film.

The method may use solid films resistant to relatively high or low temperatures, or films of materials resistant to certain chemicals.

The solid films may be opaque, translucent, coloured or metallized. A metallized film may be required for infrared inspection. Such film can "modify" the surface to result in its improved spectral performance.

Solid films of the invention may include a printed, embossed or embedded grid, reference, alignment or marking system.

The films can bridge holes and damaged areas.

Furthermore, the invention provides an apparatus for preparing a solid surface, or surface of a solid object, for instrumental inspection. The apparatus comprises a sheet of a solid, deformable film, holding means for holding the sheet against a selected solid surface to be inspected, and means for forcing the sheet against the surface (or a part thereof) to achieve a controlled contiguous relationship therebetween.

The holding means may be embodied by a frame or a casing on which the film is spread and attached to at its periphery. The forcing means may include positive pressure means, negative pressure means, electrostatic attraction means, elastic properties of the film (enhanced by shrink wrapping), or a mechanical force.

DETAILED DESCRIPTION OF THE INVENTION

Because of a plurality of types of inspected objects and their surfaces and a number of requirements associated with specific inspection methods, it is not possible to discuss a single embodiment of the method as a preferable embodiment. Instead, it will be appreciated that a specific version of the method, and of the apparatus as applicable would have to be selected for a particular application. Therefore, a number of embodiments of the invention, illustrative of the method as well as of the apparatus, is described and explained below, the invention still not being limited thereto.

Figure 1:
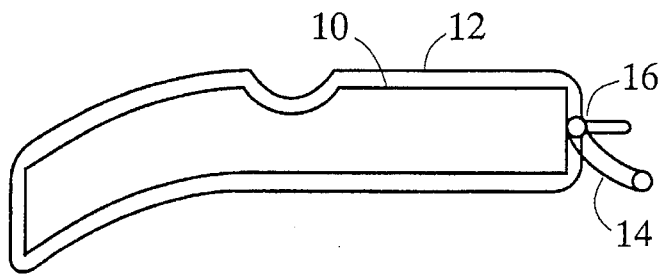
FIG. 1 illustrates an embodiment of the invention in which the subject surface is enclosed in a bag of solid film, the bag being evacuated to bring the film into conformity with the surface.

Turning now to the drawings, FIG. 1 shows an object 10 wrapped in a bag 12 made of a homogeneous, non-perforated polymeric film and equipped with a tubing 14 and a valve 16, the tubing connecting the interior of the bag with a source of negative pressure, not shown in the drawing.

To clarify the definition of contiguity, when most of the air is evacuated from the bag via the external vacuum source, the resulting pressure differential assures the conformity of the film to the inspected surface; small irregularities of the surface will be bridged to a degree depending on the rigidity and thickness of the film and the level of the negative pressure. Assuming that the pressure and temperature are maintained substantially uniform for the time of the inspection, controlled conditions are provided for the inspection. Following the inspection, the bag can be re-pressurized and removed from the object, leaving it in the original condition while the bag can be reused.

Figure 2:
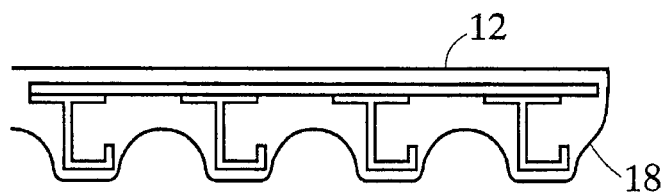
FIG. 2 shows a similar embodiment as in FIG. 1 wherein at least a part of the bag is of a puncture/tear resistant material.

In FIG. 2, a part 18 of the vacuum bag 12 is made of a different material than the solid film to afford puncture and tear resistance.

Figure 3:
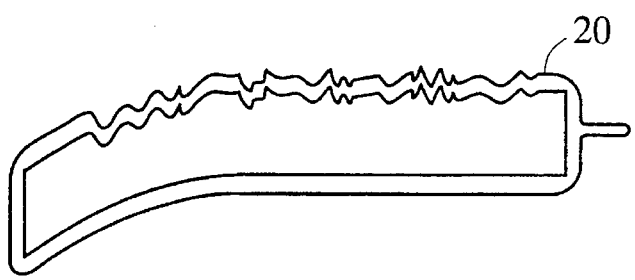
FIG. 3 shows an embodiment in which the solid film retains the surface features of the object for a deferred inspection.

The use of a metal foil 20 (FIG. 3) permits the user to obtain a replica of the subject surface. The replica may then be put aside for a deferred inspection not necessitating the real object. A metal foil is also a preferable choice when elevated temperatures are involved.

Figure 4:
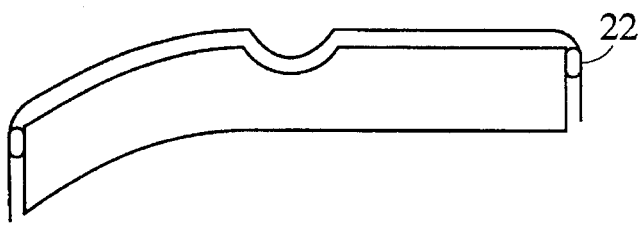
FIG. 4 illustrates the application of a vacuum edge seal.

When only a part of the surface is subject to inspection, a mechanical seal 22 may be employed to "cordon off" a part of the film and to provide a reduced pressure in the sealed-off area, as shown in FIG. 4.

Figure 5:
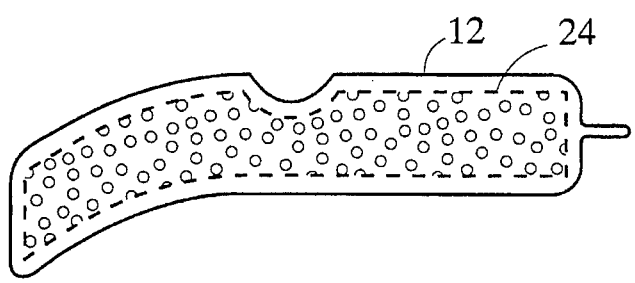
FIG. 5 shows the application of the invention for a porous material.

Referring to FIG. 5, the film 12 can bridge pores 24 and cover the roughness of the surface thus providing a smoother surface for inspection, if desired. Needless to say, the reverse can also be arranged for in that a rough or embossed film is applied to a relatively smooth surface to modify the signal of the surface on inspection.

Figure 6:
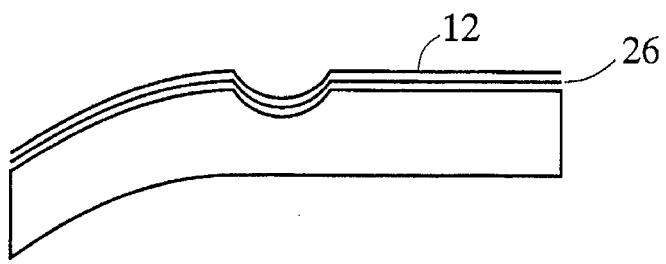
FIG. 6 illustrates the use of an adhesive to achieve the contiguity between the film and the surface.

An adhesive backing may also be employed to achieve the purpose of the invention. To that effect, a film with a releasable-adhesive backing may be placed over the surface and forced against it. Alternatively, a separate layer of releasable adhesive 26, sprayed or in a film form, can be applied onto the subject surface prior to the application of the external film 12 (FIG. 6).

Figure 7:
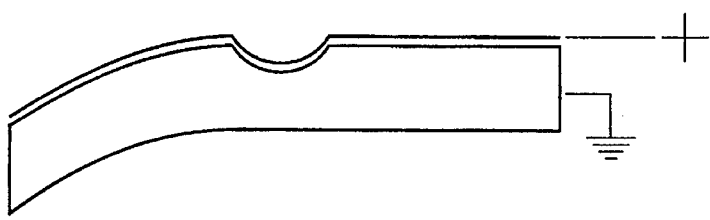
FIG. 7 is an illustration of the use of electrostatic attraction for the purposes of the invention.
Figure 8:
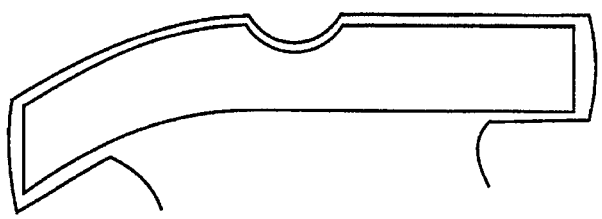
FIG. 8 illustrates the use of shrink wrapping for the purposes of the invention.

Electrostatic attraction (FIG. 7) and shrink wrapping (FIG. 8) are other embodiments of the method of the invention.

Figure 9:
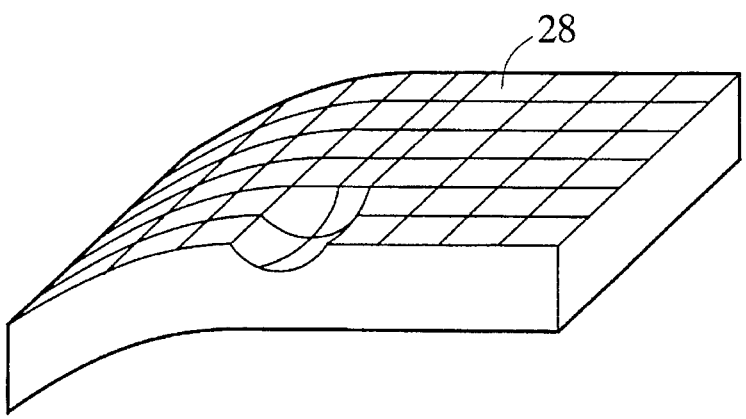
FIG. 9 shows a film of the invention incorporating a reference grid.

FIG. 9 illustrates the use of a solid film with an embossed, embedded or printed grid 28 for surface characteristics location purposes.

Figure 10:
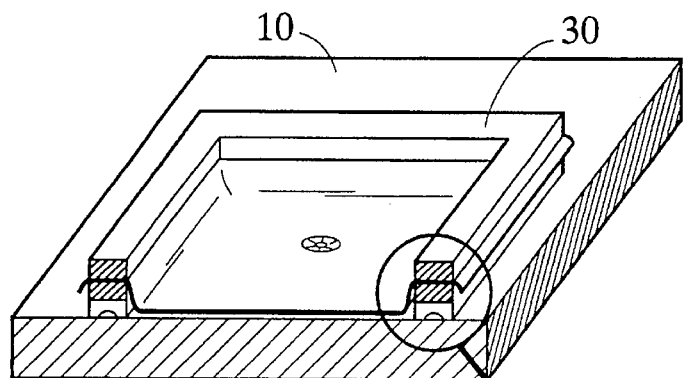
FIG. 10 is a view of the apparatus of the invention operating with vacuum.

FIG. 10 illustrates an embodiment of the apparatus of the invention. A travelling frame 30, shown in a cross-section, is adapted to be placed over the surface 10 to be inspected. To the frame is fastened a sheet of a polymeric film 12. The frame 30 is provided with a rubber seal 32 adapted to conform to a selected area of the surface 10. A vacuum tubing 34 is located in the frame so as to connect the area bordered by the film 12, the surface 10 and the frame 30 along with the seal 32, with a source of vacuum, not illustrated. An inspection equipment, not part of the invention, may be positioned separately above the surface to be inspected or may be mounted onto the frame 30.

Figure 11:
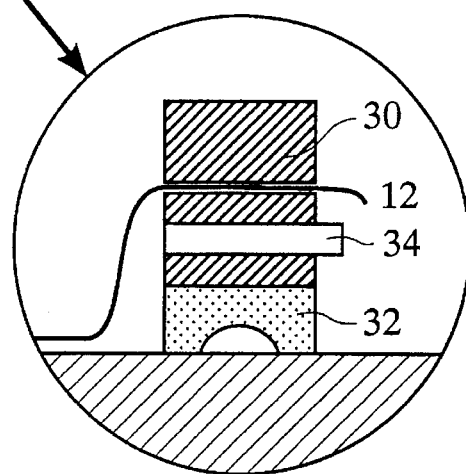
FIG. 11 is a view of another embodiment of the apparatus of the invention, operating with positive pressure.
Figure 11:
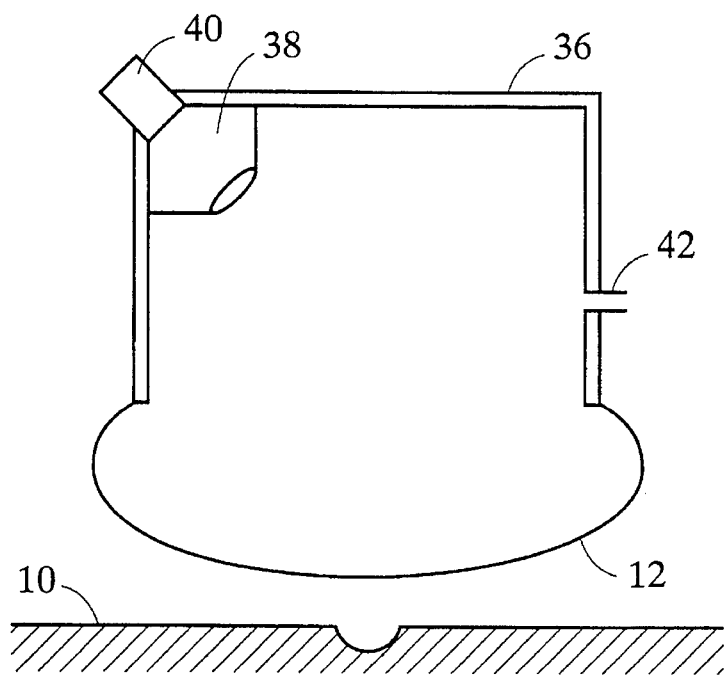

FIG. 11 illustrates another embodiment of the apparatus of the invention. A casing, or box 36 is equipped with an inspection instrument 38 with its sensor 40 being accessible by the user from outside of the casing 36. A polymeric film 12 is fastened to the edges of the casing 36 so as to enclose hermetically the inside of the casing. A piece of tubing 42 is provided to connect the inside of the casing 36 with a source of positive pressure, not illustrated.

In operation, a constant positive pressure is maintained inside the casing 36 forcing the film 12 to bulge outwardly so as to create a bladder. The casing with the bladder is then positioned over and held against a selected area of the surface 10 while the inspection is being conducted.

The film material should be tough enough to resist tearing. Its internal surface may be provided with a suitable coating to assist the specific inspection technique. Similarly as in embodiments illustrated in FIGS. 1, 4, 5, 7, 9 and 10, the film of FIG. 11 is reusable and so is the apparatus of FIGS. 10 and 11 subject to the shape and area of the surface to be inspected.

While the invention employs known techniques such as shrink wrapping, the use of those techniques for the purposes of instrumental inspection as described hereinabove is quite remote from the field of e.g. packaging where shrink wrapping is commonly used.

While the invention has been particularly described with reference to preferred embodiments thereof, it will be understood by those skilled in the art that various changes in form and detail may be made therein without departing from the spirit and scope of the invention.

We claim:

1. A method of preparing the surface of a solid object for instrumental optical inspection, the method consisting of:
   a) applying a layer of a solid, deformable film to the surface to be inspected, and
   b) bringing said layer and said surface or a part thereof into a controlled contiguous releasable relationship to modify the optical response of said surface wherein the contiguity is achieved by way of negative pressure applied between said film and said surface.

2. A method of preparing the surface of a solid object for instrumental optical inspection, the method consisting of:
   a) applying a layer of a solid, deformable film to the surface to be inspected, and
   b) bringing said layer and said surface or a part thereof into a controlled contiguous releasable relationship to modify the optical response of said surface wherein the contiguity is achieved by the use of an adhesive applied between said film and said surface.

3. The method of claim 2 wherein the adhesive is a releasable adhesive.

4. A method of preparing the surface of a solid object for instrumental optical inspection, the method consisting of:
   a) applying a layer of a solid, deformable film to the surface to be inspected, and
   b) bringing said layer and said surface or a part thereof into a controlled contiguous releasable relationship to modify the optical response of said surface wherein the contiguity is achieved by means of electrostatic force.

5. A method of preparing the surface of a solid object for instrumental optical inspection, the method consisting of:
   a) applying a layer of a solid, deformable film to the surface to be inspected, and
   b) bringing said layer and said surface or a part thereof into a controlled contiguous releasable relationship to modify the optical response of said surface wherein the contiguity is achieved by means of shrink wrapping.

* * * * *